US007289840B2

(12) United States Patent
Norfray

(10) Patent No.: US 7,289,840 B2
(45) Date of Patent: Oct. 30, 2007

(54) METHOD FOR MONITORING EARLY TREATMENT RESPONSE

(75) Inventor: Joseph F. Norfray, Glenview, IL (US)

(73) Assignee: Receptomon, LLC, Glenview, IL (US)

( * ) Notice: Subject to any disclaimer, the term of this patent is extended or adjusted under 35 U.S.C. 154(b) by 255 days.

(21) Appl. No.: 10/946,741

(22) Filed: Sep. 22, 2004

(65) Prior Publication Data

US 2006/0064003 A1 Mar. 23, 2006

(51) Int. Cl.
*A61B 5/05* (2006.01)
(52) U.S. Cl. ...................................... 600/410; 424/9.3
(58) Field of Classification Search ................ 600/407, 600/410; 324/307, 309; 424/1.89, 9.3
See application file for complete search history.

(56) References Cited

U.S. PATENT DOCUMENTS

| | | | |
|---|---|---|---|
| 4,354,499 A | 10/1982 | Damadian | |
| 4,411,270 A | 10/1983 | Damadian | |
| RE32,619 E | 3/1988 | Damadian | |
| RE32,689 E | 6/1988 | Damadian | |
| 4,843,321 A | 6/1989 | Sotak | |
| 4,962,357 A | 10/1990 | Sotak | |
| 5,111,819 A | 5/1992 | Hurd | |
| 5,200,345 A | 4/1993 | Young | |
| 5,578,921 A | 11/1996 | Morrell | |
| 5,585,118 A * | 12/1996 | Stoll | 424/488 |
| 5,617,861 A | 4/1997 | Ross et al. | |
| 5,887,588 A | 3/1999 | Usenius et al. | |
| 5,903,149 A * | 5/1999 | Gonen et al. | 324/307 |
| 6,046,589 A | 4/2000 | Lamerichs et al. | |
| 6,181,134 B1 | 1/2001 | Wald | |
| 6,280,383 B1 | 8/2001 | Damadian | |
| 6,347,239 B1 | 2/2002 | Arnold et al. | |
| 6,400,150 B1 | 6/2002 | Liu et al. | |
| 6,617,169 B2 | 9/2003 | Ke et al. | |
| 6,630,125 B2 * | 10/2003 | DeGrado et al. | 424/1.89 |
| 6,639,405 B2 | 10/2003 | Liu et al. | |
| 6,681,132 B1 | 1/2004 | Katz et al. | |
| 6,708,053 B1 | 3/2004 | Brooks et al. | |
| 6,756,063 B2 * | 6/2004 | Kiss | 424/630 |
| 2001/0003423 A1 | 6/2001 | Wald | |
| 2002/0142367 A1 | 10/2002 | Ke et al. | |
| 2002/0173713 A1 | 11/2002 | Pfefferbaum et al. | |
| 2003/0028093 A1 | 2/2003 | Ke et al. | |
| 2003/0199751 A1 | 10/2003 | Gonzalez et al. | |
| 2003/0208120 A1 | 11/2003 | Thomas et al. | |
| 2003/0214292 A1 | 11/2003 | Heid et al. | |
| 2004/0092809 A1 | 5/2004 | DeCharms | |
| 2005/0107683 A1* | 5/2005 | Mountford et al. | 600/410 |
| 2006/0035945 A1* | 2/2006 | Attardo et al. | 514/365 |
| 2006/0177377 A1* | 8/2006 | Norfray | 424/9.3 |
| 2006/0177378 A1* | 8/2006 | Norfray | 424/9.3 |

OTHER PUBLICATIONS

Negendank, "Studies of Human Tumors by MRS: a Review," NMR In Biomedicine, vol. 5, pp. 303-324 (1992).
Harrigan, "Angiogenic Factors in the Central Nervous System," Neurosurgery, vol. 53, No. 3, pp. 639-660 (2003).
Negendank, "Proceedings of a National Cancer Institute Workshop: MR Spectroscopy and Tumor Cell Biology," Radiology, vol. 185, pp. 875-883 (1992).
Evelhoch, "Response-specific Adriamycin Sensitivity Markers Provided in in Vivo $^{31}$P Nuclear Magnetic Resonance Spectroscopy in Murine Mammary Adenocarcinomas[1]," Cancer Research, vol. 47, pp. 3396-3401 (1987).
Ruiz-Cabello, "Phospholipid Metabolites as Indicators of Cancer Cell Function," NMR in Biomedicine, vol. 5, pp. 226-233 (1992).
Ross, "The Biochemistry of Living Tissues: Examination by MRS," (1992).
Ross et al., "Metabolic Response of Glioblastoma to Adoptive Immunotherapy: Detection by Phosphorus MR Spectroscopy," Journal of Computer Assisted Tomography, vol. 13, No. 2, pp. 189-193, (1989).
Norfray et al., "Clinical Impact of MR Spectroscopy When MR Imaging Is Indeterminate for Pediatric Brian Tumors," AJR, vol. 173, pp. 119-125, (1999).
Norfray et al., "Alzheimer's Disease: Neuropathologic Findings and Recent Advances in Imaging," AJR, vol. 182, No. 3, pp. 3-13, (2004).
Ross et al,, "Osteosarcoma and Other Neoplasms of Bone," Arch Surg., vol. 122, pp. 1464-1469, (1987).
Griffiths et al., "$^{31}$P-NMR Studies of a Human Tumour in Situ," The Lancet, pp. 1435-1436, (1983).
Norfray et al., "Short TE Proton MRS and Neurofibromatosis Type 1 Intracranial Lesions," Journal of Computer Assisted Tomography, vol. 23, No. 6, pp. 994-1003 (1999).
Norfray, et al., "Magnetic Resonance Spectroscopy," in Pediatric Neurosurgery, 4th Edition, McLone (ed), pp. 1189-1203 (2001).
Ross et al., "Monitoring Response to Chemotherapy of Intact Human Tumours by $^{31}$P Nuclear Magnetic Resonance," The Lancet, pp. 641-646 (1984).
Norfray et al., "Monitoring Treatment Response with Choline Molecular Imaging," ARRS Annual Meeting, May 4-9, 2003. 1 page Abstract.

(Continued)

*Primary Examiner*—Brian L. Casler
*Assistant Examiner*—Baisakhi Roy
(74) *Attorney, Agent, or Firm*—Leydig, Voit & Mayer, Ltd.

(57) ABSTRACT

Disclosed is a method for monitoring early treatment response of a cancer treatment comprising measuring by magnetic resonance spectroscopy (MRS), for example, proton MRS, the amount of Choline present in the cancerous tissue before and after treatment; the treatment comprises administration of a cell surface receptor inhibitor, for example, an EGFR inhibitor, whereby a decrease in the amount of Choline after treatment is indicative of a positive response. The decrease in the amount of Choline represents the decrease in the internal cell membrane as a result of down regulation of the organelles and their secretory granules and their transport vesicles. Disclosed also is a method for determining effectiveness of a cell surface receptor inhibitor in the treatment of cancer.

30 Claims, No Drawings

OTHER PUBLICATIONS

Schwarz et al., "Early in vivo Detection of Metabolic Response: A Pilot Study of $^1$H MR Spectroscopy in Extracranial Lymphoma and Germ Cell Tumours," The British Journal of Radiology, pp. 959-966 (2002).

Erlich, "Cancer Drug Development: New Directions and Challenges—Smi Conference," Idrugs, vol. 6, No. 4, pp. 331-333 (2003).

Eliason et al., "Potential for Predicting Toxicity and Response of Fluoropyrimidines in Patients," Current Drug Targets, vol. 5, pp. 383-388 (2004).

Matsumoto et al., "Bax to Bcl-2 Ratio and Ki-67 Index are Useful Predictors of Neoadjuvant Chemoradiation Therapy in Bladder Cancer," Jpn. J. Clin. Oncol, vol. 34, No. 3, pp. 124-130 (2004).

Fujimoto et al., A new immunological parameter predicting the efficacy of cancer therapy, Editorial, Annals of Cancer Research and Therapy, vol. 7, No. 2 (Title Only).

Fujimoto et al., Involvement of Tumor-specific CD4 and CD8 Suppressor T Cell (Ts) Lines in Down-regulation of Anti-tumor Immunity to a Murine Syngeneic Sarcoma, The 11th International Congress of Immunology 2001 (Abstract).

Abstract, AR Bianco et al., British Journal of Cancer, vol. 89, (Suppl. 2) (2003). S25-S35.

Abstract, M. Boyer, British Journal of Cancer, vol. 89, (Suppl. 2) (2003). S25-S35.

Abstract, F. Cappuzzo et al. I, British Journal of Cancer, vol. 89, (Supp. 2) (2003). S25-S35.

Abstract, F. Cappuzzo et al. II, British Journal of Cancer, vol. 89, (Suppl. 2) (2003). S25-S35.

Abstract, F de Braud et al., British Journal of Cancer, vol. 89, (Suppl. 2) (2003). S25-S35.

Abstract J de la Cruz et al. I, British Journal of Cancer, vol. 89, (Suppl. 2) (2003). S25-S35.

Abstract, J de la Cruz et al. II British Journal of Cancer, vol. 89, (Suppl. 2) (2003). S25-S35.

Abstract, K de Leeuw et al., British Journal of Cancer, vol. 89, (Suppl. 2) (2003). S25-S35.

Abstract, E. Diaz-Canton, British Journal of Cancer, vol. 89, (Suppl. 2) (2003). S25-S35.

Abstract, DM Kowalski et al., British Journal of Cancer, vol. 89, (Suppl. 2) (2003). S25-S35.

Abstract, P. Maione et al., British Journal of Cancer, vol. 89, (Suppl. 2) (2003). S25-S35.

Abstract, A. Mancuso et al., British Journal of Cancer, vol. 89, (Suppl. 2) (2003). S25-S35.

Absract, S. Martin-Algarra et al., British Journal of Cancer, vol. 89, (Suppl. 2) (2003). S25-S35.

Abstract, JL Martinez, British Journal of Cancer, vol. 89, (Suppl. 2) (2003). S25-S35.

Abstract, E. Razis et al., British Journal of Cancer, vol. 89, (Suppl. 2) (2003). S25-S35.

Abstract, M. Reck et al., British Journal of Cancer, vol. 89, (Suppl. 2) (2003). S25-S35.

Abstract, BN Stein et al., British Journal of Cancer, vol. 89, (Suppl. 2) (2003). S25-S35.

Abstract, R van der Kamp et al., British Journal of Cancer, vol. 89, (Suppl. 2) (2003). S25-S35.

Abstract, N. van Zandwijk I, British Journal of Cancer, vol. 89, (Suppl. 2) (2003). S25-S35.

Abstract, N. van Zandwijk II, British Journal of Cancer, vol. 89, (Suppl. 2) (2003). S25-S35.

Abstract, MD Vincent, British Journal of Cancer, vol. 89, (Suppl. 2) (2003). S25-S35.

Blackledge, G. et al., "Gefitinib ('Iressa', ZD1839) and new epidermal growth factor receptor inhibitors," British Journal of Cancer (2004) 90, 566-572.

Ranson, M. et al., "ZD1839, a Selective Oral Epidermal . . . Results of a Phase I Trial," Journal of Clinical Oncology, vol. 20, No. 9 (May 1, 2002: pp. 2240-2250).

Katz, A. et al., "Quality-of-life benefits and evidence of antitumour activity for patients with brain metastases treated with gefitinib," British Journal of Cancer, vol. 89 (2003).

Fulham et al., "Mapping of Brain Tumor Metabolites with Proton MR Spectroscopic Imaging: Clinical Relevance[1]," Radiology, vol. 185, No. 3, pp. 675-686 (1992).

Lynch et al., "Activating Mutations in the Epidermal Growth Factor Receptor Underlying Responsiveness of Non-Small-Cell Lung Cancer to Gefitinib," New England Journal of Medicine, vol. 350, No. 21, pp. 2129-2139 (2004).

U.S. Appl. No. 11/053,059, filed Feb. 8, 2005, Norfray.

U.S. Appl. No. 11/193,037, filed Jul. 29, 2005, Norfray.

Balkwill et al., *The Lancet*, 357, 539-545 (2001).

Bluml et al., *Magn. Reson. Med.*, 42, 643-654 (1999).

Colman, *Semin. Thromb. Hemost.*, 30(1), 45-61 (2004).

Danielsen et al., *Magnetic Resonance Spectroscopy Diagnosis of Neurological Diseases*, Marcel Dekker, Inc. Ch.3: The clinical significance of metabolites, 23-43 (1999).

DeClerck et al., *Am. J. Pathol.*, 164(4), 1131-1139 (Apr. 2004).

Engelse et al., *Semin. Thromb. Hemost.*, 30(1), 71-82 (2004).

Fernandez et al., *Semin. Thromb. Hemost.*, 30(1), 31-44 (2004).

Fisher et al., *Neuroimg. Clin. N. Am.* 12, 477-499 (2002).

Jin et al., *Br. J. Cancer*, 90, 561-565 (2004).

Kreis et al., *J. Magnetic Resonance Series B*, 102, 9-19 (1993).

Nie et al., *Semin, Thromb. Hemost.* 30(1), 119-125 (2004).

Podo, *NMR in Biomedicine*, 12, 413-429 (1999).

Ross et al., *Magnetic Resonance Quarterly*, 10, 191-247 (1994).

Sierko et al., *Semin. Thromb. Hemost.*, 30(1), 95-108 (2004).

Tang et al., Semin. Thromb. Hemost. *30*, 109-117 (2004).

Wojtukiewicz et al., *Semin. Thromb. Hemost.* 30(1), 145-156 (2004).

Yu et al., *Semin. Thromb. Hemost.* 30(1), 21-30 (2004).

Becker, Wayne M. et al., Intracellular Compartments: "The endoplasmic reticulum, Golgi complex, lysosomes, and peroxisomes," *The World of the Cell, Third Edition*, The Benjamin/Cummings Publishing Company, Ch. 9, pp. 229-270, (1996).

Dzik-Jurasz, A., "Angiogenesis imaging In man: a personal view from the pharmaceutical Industry," *The British Journal of Radiology*, Special Issue 2003, pp. S81-S82 (2003).

Encyclopaedia Britannica, "Cells: Their structures and functions," *The New Encyclopaedia Britannica*, V. 15, Macropaedia, 15th edition, pp. 565-593 (1994).

Fukuoka, Masahiro et al., "Multi-institutional randomized Phase II trial of Gefitinib for previously treated patients with advanced non-small-cell lung cancer," *Journal of Clinical Oncology*, vol. 21, No. 12 (Jun. 15, 2003): pp. 2237-2246 DOI: 10.1200/JCO.2003.10.038.

Fuller, Gerald M. et al., "Organelles and vesicle traffic," *Molecular Basis of Medical Cell Biology* (a Lange medical book), Ch. 4, pp. 67-92 (1998).

Galbraith, S. M., "Antivascular cancer treatments: Imaging biomarkers in pharmaceutical drug development," *The British Journal of Radiology*, 76 (2003), S83-S86 DOI: 10,1259/bjr/15255885.

International Searching Authority, "International search report" and "Written opinion of the International Searching Authority," for International Application No. PCT/US05/27060, mailed Jan. 24, 2007.

Kauppinen, Risto A., "Monitoring cytotoxic tumour treatment response by diffusion magnetic resonance imaging and proton spectroscopy," NMR Biomedicine, NMR Biomed. 2002:15:6-17; DOI:10,1002/nbm.742.

Leach, M. O. et al., The assessment of antiangiogenic and antivascular therapies in early-stage clinical trials using magnetic resonance imaging; issues and recommendations, *British Journal of Cancer* (2005) 92 (9), pp. 1599-1610.

Nakagami, Katsunao et al., "Increased choline kinase activity and elevated phosphocholine levels in human colon cancer," Jpn. J. Cancer Res. 90, 419-424, Apr. 1999.

Pollard, Thomas D., "Programmed cell death," *Cell Biology*, Elsevier, Inc., Ch. 49, pp. 767-782 (2004); ISBN 1-4160-2388-7.

Wojtukiewicz, Marek Z. et al., Contribution of the hemostatic system to angiogenesis in cancer; *Seminars in Thrombosis and Hemostasis*, vol. 30, No. 1, (2004) pp. 5-20.

Fujimoto et al., A new immunological parameter predicting the efficacy of cancer therapy, Editorial, Annals of Cancer Research and Therapy, vol. 7, No. 2 (Title Only), undated.

Abstract, A. Chioni et al., British Journal of Cancer, vol. 89, (Suppl. 2) (2003). S25-S35.

Abstract, H. Cortes-Funes et al., British Journal of Cancer, vol. 89, (Suppl. 2) (2003). S25-S35.

Abstract, B. Dieriks et al., British Journal of Cancer, vol. 89, (Suppl. 2) (2003). S25-S35.

Abstract, A. Gelibter et al., British Journal of Cancer, vol. 89, (Suppl. 2) (2003). S25-S35.

Abstract, R. Gervais et al., British Journal of Cancer, vol. 89, (Suppl. 2) (2003). S25- S35.

Abstract, V. Petersen et al., British Journal of Cancer, vol. 89, (Suppl. 2) (2003). S25-S35.

Abstract, L. Petruzelka et al. I, British Journal of Cancer, vol. 89, (Suppl. 2) (2003). S25-S35.

Abstract, L. Petruzelka et al. II, British Journal of Cancer, vol. 89, (Suppl. 2) (2003). S25-S35.

* cited by examiner

METHOD FOR MONITORING EARLY TREATMENT RESPONSE

FIELD OF THE INVENTION

This invention pertains to a method for monitoring early response to cancer treatment, particularly in a treatment involving cell surface receptor inhibitors. The method involves the use of Magnetic Resonance Spectroscopy (MRS).

BACKGROUND OF THE INVENTION

Some of the common approaches to cancer treatment include surgery, radiation therapy, and chemotherapy. Radiation therapy and chemotherapy are effective if they are capable of killing the tumor cells; i.e., when they act as cytotoxic agents. Typically, the response to radiation therapy or chemotherapy is monitored by magnetic resonance imaging (MRI) of the tumor, wherein a decrease in tumor size is indicative of positive response to treatment.

MRS has been proposed as a tool for obtaining information on cellular metabolism; see, for example, Norfray, J. et al., Ch. 110 in *Pediatric Neurosurgery*, 4$^{th}$ ed., McLone, D. G., et al. (Eds), W.B. Saunders Co. (2001). MRS also has been proposed for diagnosing the treatment response of tumors with cytotoxic agents; see, for example, Fulham, M. J., et al., *Radiology*, 185, 675-686 (1992), which discloses that brain tumor metabolism was studied with $^1$H MRS before and after treatment with radiation therapy. MRS permits non-invasive examination of metabolic characteristics of human cancers in a clinical environment. Accessible nuclei include $^{31}$P, $^{13}$C, $^1$H, and $^{23}$Na. $^{31}$P MRS contains information about energy status (phosphocreatine, inorganic phosphate, and nucleoside triphosphates), phospholipids metabolites (phosphomonoesters and phosphodiesters), intracellular pH (pH NMR), and free cellular magnesium concentration ($Mg^{2+}$ f). Water-suppressed $^1$H MRS shows total choline, total creatine, lipids, glutamate, inositols, lactate, and the like. Negendank, W., *NMR in Biomedicine*, 5, 303-324 (1992).

Further, U.S. Pat. No. 6,681,132 (Katz et al.) discloses a method for determining the effectiveness of chemotherapy comprising administering a dose of a cytotoxic antineoplastic agent to a subject prior to surgical removal of a cancerous tumor, acquiring magnetic resonance data from the subject, and determining whether the treatment has affected the population of a nuclei, particularly $^{23}$Na. Negendank, W., supra, provides a review of various studies of human tumors by MRS.

See also Ross, B. et al., *The Lancet*, 641-646 (1984) discusses monitoring response to cytotoxic chemotherapy of intact human tumors by $^{31}$P MRS; Griffiths, J. R. et al., *The Lancet*, 1435-36, Jun. 25, 1983 discloses the use of $^{31}$P MRS to follow the progress of a human tumor during chemotherapy with doxorubicin; Ross, B. et al., *Arch. Surg.*, 122, 1464-69 (1987) discloses the monitoring of chemotherapeutic treatment response of osteosarcoma and other neoplasms of the bone by $^{31}$P MRS; and Norfray, J. F. et al., *J. Computer Assisted Tomography*, 23(6), 994-1003 (1999) discloses an MRS study of the neurofibromatosis type 1 intracranial lesions.

More recently, peptide inhibitors, e.g., cell surface receptor inhibitors have been proposed for cancer treatment. See, for example, Blackledge, G. et al., *British J. Cancer*, 90, 566-572 (2004), which discloses that the epidermal growth factor receptor (EGFR) is a promising target for cancer therapy and that most advanced in development are the EGFR tyrosine kinase inhibitors (TKI's) gefitinib (Iressa, ZD 1839) and erlotinib (Tarceva, OSI-774), and the monoclonal antibody cetuximab (Erbitux, IMC-C225); Katz, A. et al., *British J. Cancer*, 89 (suppl. 2) S15-S18 (2003), which discloses the quality-of-life benefits and evidence of antitumor activity for patients with brain metastases treated with gefitinib; and Ranson, M. et al., *J. Clin. Oncol.*, 20, 2240-50 (2002) which discloses that gefitinib is well tolerated and active in patients with solid, malignant tumors. However, the peptide receptor inhibitors have a positive response in only 15 to 50% of the patients treated.

The peptide inhibitors are cytostatic rather than cytotoxic; accordingly, classical signs of treatment response, e.g., decreased tumor size or decreased enhancement, common with cytotoxic agents, may not be present with cytostatic peptide inhibitors. Accordingly, classical imaging techniques such as MRI alone may not be suitable or adequate to monitor treatment response.

While MRS is effective as a tool for monitoring treatment response, the disclosures in the art show that it has been applied to monitor the response to cytotoxic agents (radiation and chemotherapy). In many cases, a detectable change in tumor size is observed only after a significantly long period of time, for example, after treatment for a period of about 3 months or more. Such long periods of time could be harmful to the patient, especially if the treatment has not been effective or only partially effective, such as, for example, treatments involving the use of peptide inhibitors; during this long period of time, tumor cells could multiply or metastasize, and lead to worsening of the patient's condition.

The foregoing shows that there exists a need for a method where an early treatment response can be monitored, especially where the treatment involves cell surface receptor inhibitors. Accordingly, the present invention provides such a method. This and other advantages of the invention, as well as additional inventive features, will be apparent from the description of the invention provided herein.

BRIEF SUMMARY OF THE INVENTION

The invention provides a method for monitoring early treatment response of a cancer treatment comprising measuring by MRS, the amount of Choline present in the cancerous tissue before and after treatment; the treatment comprises administration of a cell surface receptor inhibitor, whereby a decrease in the amount of Choline after treatment is indicative of a positive response. In accordance with the invention, diagnosed cancers can be monitored by following cell membrane metabolism utilizing the Choline peak on $^1$H MR spectroscopy. The Choline peak represents the visible mobile Choline forming the plasma and organelle cell membranes. A decrease in the Choline identifies treatment response; an increase in the Choline peak identifies treatment failure.

The present invention provides several advantages, for example, the amount of Choline changes prior to classical imaging findings, and the MRS peak corresponding to Choline changes even with a treatment based on cytostatic peptide inhibitors. The present invention offers the combined advantages of MRI and MRS and provides a method to monitor early treatment response. The present invention also provides a method for monitoring cancer treatment.

DETAILED DESCRIPTION OF THE INVENTION

The present invention is predicated on monitoring changes in the amount of one or more metabolites occurring in an internal cell membrane, for example, changes induced by the down regulation of one or more of the intracellular organelles and their secretory granules and transport vesicles. The internal cell membranes, which constitute nearly 90% of the total cell membranes, form the membranes of the nucleus, the mitochondria, the lysosomes, the peroxisomes, the endoplasmic reticulums, the Golgi apparatus, the secretory granules, and the transport vesicles. The cell surface receptor inhibitors down-regulate the intracellular organelles and their secretory granules and transport vesicles.

Accordingly, the present invention provides a method for monitoring early treatment response of a cancer treatment comprising measuring, by Magnetic Resonance Spectroscopy (MRS), the amount of Choline present in the cancerous tissue before and after treatment; the treatment comprises administration of a cell surface receptor inhibitor, whereby a decrease in the amount of Choline after treatment is indicative of a positive response. MRS can be based on the resonance of any suitable nuclei; for example, nuclei selected from the group consisting of $^{31}P$, $^{1}H$, $^{13}C$, and $^{23}Na$, and any combination thereof; preferably, $^{1}H$.

A decrease in the amount of Choline occurs very early as a result of the down-regulation. Since Choline contains 9 protons per molecule (as trimethylamines or trimethylammonium salts), the Choline signal is amplified nine-fold. Since up to 90% of the cell membranes can be down regulated in a tumor, MRS provides a sensitive method to monitor early treatment response.

The term "Choline" herein is used to denote choline $((CH_3)_3N^+CH_2CH_2OH)$, a derivative of choline, or a combination of choline and/or one or more derivatives of choline. Examples of choline derivatives include lysophosphatidylcholine, or glycerophosphocholine, phosphomonoesters of choline (e.g., phosphocholine), phosphodiesters of choline (e.g., phosphatidylcholine), sphingomyelin, phosphoethanolamine, glycerophosphoethanolamine, or any combination thereof. In an embodiment of the invention, the term "Choline" represents the sum of choline and all choline derivatives (or total choline), for example, the sum of choline and phosphocholine. Phosphoserine and glycerophosphoserine also can be monitored Ruiz-Cabello, J. et al., *NMR in Biomedicine*, 5, 223-233 (1992); Podo, F., *NMR in Biomedicine*, 12, 413-439 (1999); and Blüms, S. et al., *Magn. Reson. Med.*, 42, 643-654 (1999).

The amount of Choline can be measured by MRS in any suitable manner. For example, the amount of Choline can be measured by measuring the height of a peak or peaks corresponding to Choline. In another embodiment, the amount of Choline can be measured by measuring the area under a peak or peaks corresponding to Choline. In yet another embodiment, the amount of Choline can be measured by measuring the ratio of the height of a peak or peaks corresponding to Choline relative to the height of a peak or peaks of an internal standard. In a further embodiment, the amount of Choline can be measured by measuring the ratio of the area under a peak or peaks corresponding to Choline relative to the area under a peak or peaks of an internal standard.

Any suitable internal standard can be used. For example, the internal standard is total creatine when the MRS is based on $^{1}H$ resonance, or internal standard is adenosine triphosphate (ATP) when the MRS is based on $^{31}P$ resonance. The term "total creatine" refers to the combination of creatine and phosphocreatine. Creatine is buffered in cell systems; accordingly, the amount of creatine remains substantially constant.

It is contemplated that the present inventive method is applicable to monitoring early treatment response wherein the treatment involves inhibition of any suitable cell surface receptor, for example, the cell surface receptor is vascular endothelial growth factor receptor (VEGFR) or epidermal growth factor receptor (EGFR), fibroblast growth factor receptor (FGFR), platelet derived growth factor receptor (PDGFR), stem cell receptor (SCFR), nerve growth factor receptor (NGFR), hepatocyte growth factor (HGFR), insulin growth factor receptor (IGFR), a receptor having a tyrosine kinase domain, a receptor having a serine threonine kinase domain, a receptor utilizing a cytoplasmic tyrosine kinase, an angiogenesis factor receptor, or integrin receptor, preferably the EGFR.

In accordance with an embodiment of the present invention, inhibition of the cell surface receptor causes an interruption in an up-regulated intracellular organelle; for example, an interruption in the function of the secretory granules and/or the transporting vesicles. In accordance with another embodiment of the invention, inhibition of the cell surface receptor causes an interruption in the function of the Golgi apparatus. In further embodiments of the invention, inhibition of the cell surface receptor causes an interruption in the function of the lysosomes, the endoplasmic reticulum, the mitochondrion, the nucleus, and/or the peroxisomes.

Examples of suitable cell surface receptor inhibitors include gefitinib, erlotinib, cetuximab, canertinib, EKB-569, lapatinib, and any combination thereof. It has been reported that gefitinib (ZD1839) is an EGFR-tyrosine kinase inhibitor (EGFR-TKI) that causes inhibition of EGF-stimulated autophosphorylation in cell lines at submicromolar concentrations. Ranson et al., supra. It has been reported that ZD1839 has demonstrated, in preclinical studies, antitumor activity against a variety of human cancer cell lines expressing EGFR, including ovarian, breast, and colon, and that it is active in a range of xenograft models, including colon cancer, non-small cell lung cancer (NSCLC), and prostate cancer. Ranson et al., supra. See also, Lynch et al., *The New England J. Medicine*, 350, 2129-2139 (May 20, 2004), which discloses that about 10% of the NSCLC patients treated with gefitinib have a rapid and often dramatic clinical response. Erlotinib is also an EGFR-TKI; it is being studied in many different cancers including breast cancer. Cetuximab is a monoclonal antibody that targets EGFR and is approved for colorectal metastatic cancer. Canertinib is also an EGFR-TKI and is targeted for cancer treatment. EKB-569 is an investigational cytostatic agent and an EGFR kinase inhibitor used to treat a variety of tumor cells that overexpress EGFR and Her2, including non-small cell lung and colorectal cancers. Lapatinib is an EGFR and ErbB-2 (Her2/neu) dual tyrosine kinase and is considered for treatment of solid tumors such as breast and lung cancer.

Protein tyrosine kinases are enzymes that provide a central switch mechanism in cellular signal transduction pathways. As such they are involved in many cellular processes such as cell proliferation, metabolism, survival, and apoptosis. Several protein tyrosine kinases are known to be activated in cancer cells and to drive tumor growth and progression. Therapeutic strategies include blocking kinase-substrate interaction, inhibiting the enzyme's adenosine triphosphate (ATP) binding site and blocking extracellular tyrosine kinase receptors on tumor cells.

The erbB or HER family of transmembrane tyrosine kinase receptors, especially receptors erbB1 (or EGFR) and erbB2 (or Her2/neu), has been identified as an important therapeutic target in a number of cancers. Her2/neu, for example, is overexpressed in around 20% to 30% of patients with aggressive breast cancer, while EGFR is overexpressed in several solid tumours.

In accordance with the present invention, any suitable cancer or tumor can be treated, for example, a cancer selected from the group consisting of brain cancer, colorectal cancer, breast cancer, acute leukemia, lung cancer, kidney cancer, squamous cell cancer, testicular cancer, stomach cancer, melanoma, sarcomas, ovarian cancer, non-small cell lung cancer, esophageal cancer, pancreatic cancer, neuroblastoma, mesothelioma, prostate cancer, bone cancer, kidney cancer, and heptocellular cancer.

In accordance with the present inventive method, early treatment response can be measured within a period of about 168 hours, preferably about 24 hours, and more preferably about 12 hours, of the treatment. For example, the response can be monitored every 12, 24, 36, 48, 60, 72, 84, 96, 108, 120, 132, 144, 156, or 168 hours, or any combination thereof, after administration of the peptide inhibitor.

The present invention also provides a method for monitoring cancer treatment comprising: (a) localizing a tumor in a patient; (b) selecting a region of interest (ROI) of the tumor; (c) obtaining magnetic resonance spectra (MRS) of the ROI; (d) measuring the amount of Choline from the MRS spectra; (e) initiating treatment comprising administering a cell surface receptor inhibitor; (f) obtaining MR spectra of the tumor at the same ROI within a period of 7 days, preferably 3 days, and more preferably within 1 day, of initiating treatment; (g) measuring the amount of Choline from the MR spectra; and (h) comparing the amount of Choline obtained before treatment with the amount of Choline obtained after treatment; whereby a decrease in the amount of Choline after treatment is indicative of a positive response to treatment.

The basis for clinical MR studies (e.g., MRS or MRI) is the one of the nuclei, for example, the hydrogen nucleus—the proton. The same machinery is used for these studies. They differ in the software manipulation of the emitted radiofrequency (RF) from the H nuclei. In MRI, the signal is used to create the image; in MRS, the signal is used to create the spectrum. Fourier Transform principle is the basis of the computer that allows the MRS software to separate the individual RFs within the signal. The spectrum therefore represents the different RFs being emitted within the selected region of interest (ROI). The points along the horizontal axis of the spectrum represent specific RFs emitted from each metabolite. The vertical axis of the spectrum is proportional to the amount of each metabolite forming the area beneath the RF peaks. Spectra can be obtained on 0.5 to 2.0T MR scanners, although high-field strength scanners provide better definition of the spectra. Spectra obtained with different-strength scanners can be compared on a scale in parts per million (ppm) along the horizontal axis because metabolites always reside at one or more specific sites, for example, alanine resides at 1.47, N-acetylaspartate resides at 2.0 and 2.6 ppm, creatine resides at 3.0 and 3.9 ppm, Choline resides at 3.2 ppm, and water resides at 5.0 ppm.

Any suitable MR spectrometer can be used in the practice of the present invention. Clinical MR spectra can be obtained on MR scanners, for example, utilizing the clinical spectroscopy package called proton brain exam/single voxel (PROBE/SV) developed by General Electric Medical Systems (Milwaukee, Wis.) for use with GE's 1.5 Tesla (T) MR scanner. See Norfray, J. et al., supra, and Norfray, J. F. et al., supra, for procedures for obtaining MR spectra, identification of the peaks corresponding to metabolites such as Choline, creatine, and others, and ratio of the peaks. See also Danielsen and Ross, Magnetic Resonance Spectroscopy Diagnosis of Neurological Diseases, Marcel Dekker, Inc. (1999); Ross, B. et al., *Magnetic Resonance Quarterly*, 10, 191-247 (1994); and Ross et al., U.S. Pat. No. 5,617,861. Based on the information in the above publications, as well as information available in the art, those of skill in the art should be able to practice the invention on all types of tumors in accordance with the present invention.

The present invention can be carried out in any suitable manner, for example, as follows. Prior to initiating a therapy on a patient, the tumor is localized. Thus, for example, magnetic resonance images (MRI's) of the tumor, e.g., brain metastasis, breast malignancy, or bone tumor, with axial, sagittal, and coronal T1 and T2 images are obtained with and without contrast. A region of interest (ROI) of tumor is selected. This can be carried out based on the MRI findings to determine the tumor volume and location to be studied. MR spectra of the ROI are obtained within the tumor utilizing short and/or long TE (echo time) pulse sequences. The spectra obtained are interpreted. The peak corresponding to Choline is identified, e.g., at a chemical shift of 3.22 ppm. Based on the Choline peak, the amount of total cellular membranes is determined from either the height of the peak or the area under the peak. An internal or external standard is identified in the ROI. An example of an internal standard is creatine or total creatine. An example of an external standard is 100% 2-(trimethylsilyl)ethanol (TSE), which may be taped to the head coil of the MR spectrometer. Kreis, R. et al., *J. Magnetic Resonance*, Series B 102, 9-19 (1993). The ratio of the Choline to the standard is calculated. The Choline to creatine ratio represents a measure of the total cell membranes within the ROI of the tumor prior to treatment.

The treatment of the tumor is initiated by administering an effective amount of the receptor inhibitor starting from time zero. The early treatment response can be monitored, for example, at 24 hours (day 1) to 168 hours (day 7), as follows. The tumor is localized utilizing the same MRI pulse sequences as prior to the treatment. The same ROI is selected within the tumor. MR spectra of the tumor are obtained utilizing the same-pulse sequences, the same TR (relaxation time), TE (echo time), phases, and frequency averages. The MR spectra are interpreted as before and the Choline to creatine ratios (e.g., height or area ratios) are calculated.

If the observed decrease in the Choline to creatine ratio is 15% or more, preferably 20% or more, and more preferably 25% or more relative to pre-treatment condition, then it can be concluded that an early response is positive and tumor regression has been achieved. The early decrease in the Choline to creatine ratio identifies a decrease in the intracellular cell membranes, for example, a decrease in the organelles and their granules and/or vesicles. If the ratio of Choline to creatine increases, e.g., a 15% or more, preferably 20% or more, and more preferably 25% or more, of an early increase in the ratio is observed, the increase identifies an increase in the intracellular membranes, for example, an increase in the organelles and their granules and/or vesicles.

The present invention further provides a method for determining effectiveness of a molecule as a drug for treating cancer comprising administering an amount of the molecule to an animal having a cancerous tissue and measuring, by Magnetic Resonance Spectroscopy, the amount of Choline present in the cancerous tissue before and after administering the molecule, wherein the molecule comprises a cell surface receptor inhibitor, whereby a decrease in the amount of Choline after administering the molecule is indicative of its effectiveness. The animals to be used in the present method can be, for example, mammals such as mice, rats, horses, guinea pigs, rabbits, dogs, cats, cows, pig, and monkeys. The amount of cell surface receptor inhibitor will vary with a number of factors, e.g., weight of the animal, type of cancer, and severity of cancer, and is within the skill of the artisan. The potential drug can be administered by any suitable route of administration, e.g., oral, aerosol, parenteral, subcutaneous, intravenous, intraarterial, intramuscular, interperitoneal, rectal, and vaginal routes. The cancer can be natural or induced. Thus, effectiveness of a potential drug can be determined within a relatively short period of time, for example, within 12-168 hours, preferably 12-24 hours.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for monitoring early treatment response of a cancer treatment comprising measuring non-invasively, by Magnetic Resonance Spectroscopy (MRS), the amount of Choline present in the cancerous tissue before and after treatment, obtaining a difference between the Choline amounts, and correlating the difference with effectiveness of the cancer treatment or lack thereof; wherein the after treatment measurement is made within a period of about 168 hours of said treatment, wherein said treatment comprises administration of a cell surface receptor inhibitor.

2. The method of claim 1, wherein the MRS is based on the resonance of nuclei selected from the group consisting of $^{31}P$, $^{1}H$, $^{13}C$, and $^{23}Na$, and any combination thereof.

3. The method of claim 2, wherein the MRS is based on $^{1}H$ resonance.

4. The method of claim 1, wherein measuring the amount of Choline comprises measuring the height of a peak corresponding to Choline.

5. The method of claim 1, wherein measuring the amount of Choline comprises measuring the area under a peak corresponding to Choline.

6. The method of claim 1, wherein measuring the amount of Choline comprises measuring the ratio of the height of a peak corresponding to Choline relative to the height of peak of an internal standard.

7. The method of claim 6, wherein the internal standard is total creatine when the MRS is based on $^{1}H$ resonance.

8. The method of claim 6, wherein the internal standard is adenosine triphosphate (ATP) when the MRS is based on $^{31}P$ resonance.

9. The method of claim 1, wherein measuring the amount of Choline comprises measuring the ratio of the area under a peak corresponding to Choline relative to the area under a peak of an internal standard.

10. The method of claim 9, wherein the MRS is based on $^{1}H$ resonance and the internal standard is total creatine.

11. The method of claim 1, wherein the cell surface receptor is vascular endothelial growth factor receptor (VEGFR) or epidermal growth factor receptor (EGFR), fibroblast growth factor receptor (FGFR), platelet derived growth factor receptor (PDGFR), stem cell receptor (SCFR), nerve growth factor receptor (NGFR), hepatocyte growth factor (HGFR), insulin growth factor receptor (IGFR), a receptor having a tyrosine kinase domain, a receptor having a serine threonine kinase domain, a receptor utilizing a cytoplasmic tyrosine kinase, an angiogenesis factor receptor, or integrin receptor.

12. The method of claim 1, wherein measuring the amount of Choline comprises measuring the amount of choline, phosphocholine, phosphatidylcholine, lysophosphatidylcholine, or glycerophosphocholine, phosphomonoesters of choline, phosphodiesters of choline, phosphoethanolamine, glycerophosphoethanolamine, or any combination thereof.

13. The method of claim 1, wherein the amount of Choline is measured within a period of about 24 hours.

14. The method of claim 1, wherein the amount of Choline is measured within about 12 hours of said treatment.

15. The method of claim 1, wherein the cell surface receptor inhibitor is selected from the group consisting of gefitinib, erlotinib, cetuximab, canertinib, EKB-569, lapatinib, and any combination thereof.

16. The method of claim 1, wherein the cancer is selected from the group consisting of brain cancer, colorectal cancer, breast cancer, acute leukemia, lung cancer, kidney cancer, squamous cell cancer, testicular cancer, stomach cancer, melanoma, sarcomas, ovarian cancer, non-small cell lung cancer, esophageal cancer, pancreatic cancer, neuroblastoma, mesothelioma, prostate cancer, bone cancer, and heptocellular cancer.

17. The method of claim 1, wherein inhibition of the cell surface receptor causes an interruption in an up-regulated intracellular organelle.

18. The method of claim 17, wherein the interruption in the up-regulated intracellular organelle takes place in the secretory granules.

19. The method of claim 17, wherein the interruption in the up-regulated intracellular organelle takes place in the transporting vesicles.

20. The method of claim 1, wherein inhibition of the cell surface receptor causes an interruption in a function of the Golgi apparatus.

21. The method of claim 1, wherein inhibition of the cell surface receptor causes an interruption in a function of the lysosomes.

22. The method of claim 1, wherein inhibition of the cell surface receptor causes an interruption in a function of the endoplasmic reticulum.

23. The method of claim 1, wherein inhibition of the cell surface receptor causes an interruption in a function of the mitochondrion.

24. The method of claim 1, wherein inhibition of the cell surface receptor causes an interruption in a function of the nucleus.

25. The method of claim 1, wherein inhibition of the cell surface receptor causes an interruption in a function of the peroxisomes.

26. A method for monitoring cancer treatment comprising:
(a) localizing a tumor in a patient; (b) selecting a region of interest (ROI) of the tumor; (c) obtaining magnetic resonance spectra (MRS) of the ROI; (d) measuring the amount of Choline from the MRS spectra; (e) initiating treatment comprising administering a cell surface receptor inhibitor; (f) obtaining MR spectra of the tumor at the same ROI within a period of 7 days of initiating treatment; (g) measuring the amount of Choline from the MR spectra; and (h) comparing the amount of Choline obtained before treatment with the amount of Choline obtained after treatment; and correlating a decrease in the amount of Choline after treatment with a positive response to treatment.

27. The method of claim 26, wherein the MR spectra of the tumor is obtained within 3 days of initiating treatment.

28. The method of claim 27, wherein the MR spectra of the tumor is obtained within 1 day of initiating treatment.

29. A method for determining effectiveness of a molecule as a drug for treating cancer comprising administering an amount of the molecule to an animal having a cancerous tissue and measuring non-invasively, by Magnetic Resonance Spectroscopy, the amount of Choline present in the cancerous tissue before and within a period of about 168 hours after administering the molecule, obtaining a difference between the Choline amounts, and correlating the difference with effectiveness of the cancer treatment or lack thereof; wherein said molecule comprises a cell surface receptor inhibitor.

30. A method for monitoring early treatment response of a cancer treatment comprising measuring non-invasively, by Magnetic Resonance Spectroscopy (MRS), the amount of Choline present in the intracellular membrane of the cancerous tissue before and after treatment, obtaining a difference between the Choline amounts, and correlating the difference with effectiveness of the cancer treatment or lack thereof; wherein the after treatment measurement is made within a period of about 168 hours of said treatment, wherein said treatment comprises administration of a cell surface receptor inhibitor.

* * * * *